United States Patent [19]

Schaeffer et al.

[11] Patent Number: 5,124,313

[45] Date of Patent: Jun. 23, 1992

[54] METHODS OF IMPROVED SKIN CARE AND THE TREATMENT OF DERMATOLOGICAL CONDITIONS

[76] Inventors: Hans A. Schaeffer, 17 Pallant Ave., Linden, N.J. 07036; Geoffrey J. Brooks, 70 Tyler Pl., South Plainfield, N.J. 07080

[21] Appl. No.: 361,021

[22] Filed: Jun. 2, 1989

[51] Int. Cl.$^5$ .................... A01N 37/18; A61K 37/00
[52] U.S. Cl. .......................................... 514/2; 514/12
[58] Field of Search ........................ 514/2, 12

[56] References Cited

U.S. PATENT DOCUMENTS 3,729,568   4/1973   Kligman ............................... 424/318
3,906,108   9/1975   Felty .................................... 424/318
4,603,146   7/1986   Kligman .............................. 514/559

OTHER PUBLICATIONS

Cosmetic Ingredient Review-Assessment Retinyl Palmitate and Retinol, J. Am. Coll. Toxicol. 6(3):282-283 (1987).
Weiss et al., J. Am. Med. Assn. (JAMA) 295(4) (Jan. 22/29, 1988).
Final Report on the Safety Assessment of Retinyl Palmitate and Retinol, Chapter 2, J. Am. Coll. Toxicol. 6(3):279-287 (1987).
Chytal et al., Vitamins and Hormones, "Cellular Vitamin A Binding Protein", Academic Press, Inc., 36:1-32 (1978).
Chytal, Hepatology, 2(2):282-287 (1982).
Chytal et al., "Cellular Retinol- and Retinoic Acid--Binding Proteins in Vitamin A Action", Fed. Proc. 38:2510-2514 (1979).
Michaelson et al., Clin, and Exp. Dermatol. 4:445-451 (1979).
Rask et al., Scand. J. Chem. Lab. Invest. 40, Suppl. 154 45-61 (1980).
Counts, J. Soc. Cosmet. Chem. 39:235-240, Jul./Aug. (1988).

*Primary Examiner*—Lester L. Lee
*Assistant Examiner*—E. J. Kraus
*Attorney, Agent, or Firm*—Darby & Darby

[57] ABSTRACT

The present invention provides methods for treating or preventing various dermatological conditions in humans, such as dry, cracked or damaged skin resulting from exposure to sunlight (ultraviolet radiation) and wind, aging effects, general skin dryness, e.g., deficient moisture content, and mild acne. These methods comprise applying an effective amount of a composition to the affected target area, the composition comprising a retinyl palmitate-polypeptide complex of apparent molecular weight of from about 5,000 to about 7,000 daltons, and an isoprenoid compound, e.g., a carotenoid such as beta-carotene.

23 Claims, No Drawings

METHODS OF IMPROVED SKIN CARE AND THE TREATMENT OF DERMATOLOGICAL CONDITIONS

FIELD OF THE INVENTION

The present invention relates to methods of improved skin care and the treatment and/or prevention of various human dermatological conditions by applying to the skin or the involved mucous membranes an effective amount of a composition comprising retinyl palmitate polypeptide complex and a isoprenoid. The dermatological conditions include skin damage due to sun (ultraviolet light), wind and general climatic exposure, aging effects (facial lines), excessive dryness and mild acne.

BACKGROUND OF THE INVENTION

Vitamin A is essential for the growth, health and life of all mammals and is required for vision, reproduction and the maintenance of differentiated epithelia in skin and mucous membranes. The naturally occurring form of Vitamin A is retinol which is a free alcohol having a chemical structure described as 3,7-dimethyl-9-(2,6,6-trimethyl-1-cyclohexen-1-yl)-2,4,6,8-nonatetraen-1-ol. Retinol can be readily esterified with palmitic or acetic acids (or other fatty acids) to form the esters retinyl palmitate or retinyl acetate, respectively.

Retinol and its esters have been employed for many decades both internally dietary supplements and topically in dermatological products, including baby products, eye makeup remover, hair products, general cosmetics, e.g., conditioners, sprays, rinses, shampoos, tonics, skin creams, blushers, face powders, makeup bases and foundations, lipstick, nail creams and lotions, and suntan products, e.g., gels, creams, and liquids (See J. Am. Coll. of. Toxicol. 6, No. 3, pp. 282-283, 1987). In all, retinol and retinyl palmitate have been employed in approximately 240 different formulations. The 13th Report of the Cosmetic Ingredient Review as published in the Journal of the American College of Toxicology, Vol. 6, No. 3, 1987, states, in summary, that "retinyl palmitate and retinol are safe as cosmetic ingredients in the present practices of use and concentration".

More recently, acidic derivatives of retinol have been introduced which are highly effective in the treatment of severe (cystic) forms of acne. All-trans-retinoic acid, also called tretinoin, is distributed by the Ortho Division of Johnson & Johnson (New Brunswick, N.J.) under the brand name RETIN-A ®, which is available in cream, gel, or liquid form and is intended for topical application only. 13-cis-Retinoic acid, also called isotretinoin, is marketed under the brand name ACCUTANE ® and is available in soft gelatin capsules for internal use from Roche Laboratories (Nutley, N.J.).

Other acidic derivatives of retinol are useful, e.g., for the treatment of severe cases of psoriasis. Such derivatives include Tegison ® (Etretinate, Roche Laboratories, Nutley, N.J.) and Fenretinide (McNeil Pharmaceuticals, Spring House, Pa.).

The use of all-trans-retinoic acid for the topical treatment of acne is disclosed in U.S. Pat. No. 3,729,568, issued Apr. 24, 1983 to Kligman. In addition, the use of Vitamin A (retinoic acid) to retard aging effects in skin are disclosed in U.S. Pat. No. 4,603,146, issued Jul. 29, 1986, also to Kligman. An acne cream emulsion of tretinoin, i.e., all trans-retinoic acid, which is stabilized by xanthan gum, is also disclosed in U.S. Pat. No. 3,906,108, issued Sep. 16, 1975 to Felty. Tretinoin has been reported to be effective for the treatment of photoaged skin as reported in the Journal of the American Medical Association, Vol. 295, No. 4, Jan. 22/29, 1988.

While encouraging results have been obtained with these acidic retinoids, the toxic side effects can be very serious. Accutane ® has given rise to extensive birth defects in children of women treated with the drug during pregnancy. Allergic responses have also been reported. Retin-A ® has also been known to produce severe skin irritation, sensitization and allergic responses. Retin-A ® has also given rise to abnormalities in rat and rabbit fetuses subsequent to topical administration of the compound to the mother. Thus, Retin-A ® should be used during pregnancy only if clearly needed. Both of these products should be used only under the direct supervision of a physician.

Since the discovery of the acidic retinoids, an intensive search has been underway for a retinoid which provides the beneficial attributes of tretinoin and isotretinoin without their toxic side effects.

SUMMARY OF THE INVENTION

The present inventors have discovered that topical products comprising an effective amount of a composition comprising a retinyl palmitate polypeptide complex and an isoprenoid can be applied to the skin, mucous membranes, lips, hair and nails resulting in general improvement of numerous conditions. These conditions include skin damage due to sun (ultraviolet light), wind and general climatic exposure, aging effects (facial lines), excessive dryness and mild acne.

DETAILED DESCRIPTION OF THE INVENTION

All literature references and patents cited in this specification are hereby incorporated by reference in their entirety.

The present invention provides a number of methods for treating and/or preventing human dermatological conditions, all of which comprise applying to the skin or mucous membrane area an effective amount of a composition comprising retinyl palmitate polypeptide complex and an isoprenoid in a suitable vehicle. The amount of this composition is effective to treat or prevent the various dermatological conditions which will now be discussed.

More particularly, the present invention provides the following methods: protection and/or treatment of human skin and mucous membranes against photodamaging effffects of sunlight; protection and/or treatment of human skin against the abrasive effects of the wind; moisturization of skin; protection of skin against the effects of aging; and treatment of mild forms of acne.

Retinyl palmitate represents an esterified form of retinol, both of which occur naturally. Briefly, the metabolic scheme for the utilization of Vitamin A in the body is as follows:

Upon ingestion by a human, retinyl esters are dispersed and emulsified in the stomach, followed by extensive hydrolysis in the intestinal lumen with the aid of an enzyme produced by the pancreas (pancreatic non-specific lipase or cholesterol esterase). The resulting retinol is solubilized in mixed micelles and absorbed by the mucosal cells of the small intestine. In the mucosal cells, the retinol is re-esterified to retinyl palmitate, then incorporated in chylomicrons and transported to the liver for storage. From the hepatic stores, the ester is mobilized, bound to a protein, called the Retinol-Binding Protein (RBP), and then transported by the plasma to the target cells.

The Retinol-Binding Protein, RBP, is a single polypeptide chain with a molecular weight of approximately 21,000. RBP serves as a transport mechanism for delivery to peripheral target tissues. At the target, a specific intracellular retinol binding protein has been identified and designated CRBP for Cellular Retinol-Binding Protein, which carries the retinol through the cell walls into the target cells (see *J. Am. Coll. Toxicol.*, Vol. 6, No. 3, pp. 279-287, 1987; *Vitamins and Hormones*, Academic Press, Inc., Vol. 36, pp. 1-32, 1978; Chytil, F., *Hepatology*, Vol. 2, No. 2, p. 282, 1982; Chytil, F., and Ong, D. E., *Fed. Proceed.*, 38: 2510-2514, 1979; Michaelsson, G., et al., *Clin. and Experimental Dermatol.*, 4: 445-451, 1979; Rask, L., et al., *Scand. J. Clin. Lab. Invest.* 40, Suppl. 154, 45-61, 1980.

The Cellular Retinol-Binding Protein, CRBP, appears to be a single polypeptide chain, having a molecular weight of approximately,14,600 daltons. CRBP facilitates the interaction of retinol with binding sites in the cell nucleus where retinol exerts its action.

Without wishing to be bound by any particular theory, the present inventors have postulated that, if retinoid compounds (e.g., retinyl palmitate; retinal and retinyl acetate) are administered typically, while bound to a protein or polypeptide, the retinoid compound will be delivered to the target cells more rapidly, and selectively. In this manner, the dosage of retinoid compound which is administered or applied topically could be reduced significantly. Concomitantly, any adverse side effects generally associated with the topical administration of retinoic acids and retinoid compounds would also be eliminated or reduced drastically (see, e.g., Counts, D. F., et al., *J. Soc. Cosmet. Chem.*, 39: 235-240, July/August 1988, for discussion of retinyl palmitate and its (irritation) effects on skin).

It is generally accepted that Vitamin A and related retinoids will increase the metabolism of fibroblasts which, in turn, stimulate the formation of collagen as well as acid mucopolysaccharides. These substances, collagen and acid mucopolysaccharides, improve the elasticity and suppleness of the skin and accelerate the healing process.

It is also generally well-known that when fibroblasts are stimulated to produce fresh collagen, the moisture retention of the skin is greatly increased. Therefore, in accordance with the present invention, the retinyl palmitatepolypeptide complex may be termed an internal moisturizer rather than an externally-applied moisturizing agent.

Unfortunately, CRBP has not been sufficiently characterized for large scale production of the purified protein necessary for widespread use as a pharmaceutical adjuvant in over-the-counter beauty or treatment aids. However, the present inventors have unexpectedly discovered that certain plant extracts contain a naturally occurring protein(s) or polypeptide(s) of apparent molecular weight of from about 5,000 to about 7,000 daltons which may act(s) in a manner similar to that of mammalian CRBP. Specifically, the inventors have discovered that certain polypeptides which occur naturally in yellow or deep green vegetables, e.g., carrots, squash, pumpkins or spinach, and fish liver oils, and the, like, can be utilized and reacted with. exogenous retinol, or retinyl palmitate in a fermentation reaction vessel to produce a composition for beneficial external topical applications.

Two requirements must be met in order transport. useful effective amounts of retinoid compound, e.g., retinyl palmitate, retinol, to a target area of treatment e.g., face, lips, nails, hair, etc. First, a carrier must be employed to transport the active ingredient to the target area, i.e., for absorption through the skin or mucous membranes. Second, the retinoid compound must be capable of binding to the binding sites in the cell nucleus where retinol, the eventual metabolic product, exerts its action as described above. After absorption and delivery, retinyl palmitate is de-esterified, breaking down to retinol and palmitic acid.

The retinyl palmitate employed in accordance with this invention is available from a number of commercial sources, e.g., Roche Laboratories, Nutley, N.J., BASF Wyandotte Corp., Wyandotte, Mich.; Rhone-Poulenc Chemical Corp., Specia, France; DESMO Chemicals and others.

Briefly, the reaction of retinyl palmitate with plant derived protein or polypeptides proceeds as follows: In a suitable fermentation vessel the commercially available pure vitamin (retinol or retinyl palmitate) is reacted at mildly elevated temperatures with an excess of finely minced carrot pulp. The reaction proceeds until no more free-state Vitamin A is detectable in the reaction mixture as determined by HPLC assay. At this point the reaction is terminated. The suspension is concentrated under vacuum, followed by spray-drying under nitrogen to a free-flowing orange powder, whose characteristics will be further described in the examples below.

The retinyl palmitate-polypeptide complex (RPPC) is a solid substance having a yellow to light orange color and a slight carrot odor. It is dispersible, but only partially soluble in water, and is partially soluble in alcohol, acetone and other organic solvents. The RPPC contains a low level of essential fatty acids (approximately 2.5% by weight), lipoproteins and carbohydrates as well as some protein-bound betacarotene. The moisture content cf the RPPC is no greater than about 7.0% by weight. Following alkaline hydrolysis and using the USP assay for retinol, RPPC typically shows an activity of not less than about 250,000 i.u. per gram.

Under these above-described conditions, an impure retinyl palmitate-polypeptide complex (RPPC) is obtained which consists of approximately 25%, by weight, of retinyl palmitate (or about 250,000 i.u. per gram) and approximately 60%, by weight, of polypeptide carrier (PC), which, in addition, contains bound water, lipoproteins, carbohydrates and other impurities. The binding site between the PC and the retinyl palmitate appears to be the ester carbonyl group of the retinyl palmitate where hydrogen bonding takes place. The molecular weight of the polypeptide complex is approximately 5,000 to about 7,000 daltons, i.e., less than the molecular weight of CRBP. Polypeptides of this size can be absorbed through the skin when topically applied.

It should be understood that the molecular weight of the retinyl palmitate-polypeptide complex may vary within a certain range due to the fact that the product is derived from natural sources which are variable themselves. However, in most instances, the molecular weight of, the retinyl palmitatepolypeptide complex (RPPC) will comprise from about 5,000 to about 7,000 daltons, although as stated above, this range may vary.

It shall be pointed out that in its natural environment, e.g., principally in carrots, squash and fish liver oils, retinol is conjugated with proteins, essential fatty acids, and associated with carbohydrates, but that these materials are removed when the vitamin is solvent extracted or cold pressed into oil. Upon molecular distillation and further purification, all traces of the co-existing substances, such as related carotenoids, are eliminated. The synthetic retinol material is, of course, completely devoid of these congeners.

In contrast and as used herein, RPPC is a conjugate in which the vitamin, retinyl palmitate is complexed with low-molecular weight plant proteins or polypeptides, and is further associated with naturally occurring carotenoids (mainly BetaCarotene), and may also include lipoproteins, essential fatty acids, and carbohydrates. Due to this unique association the vitamin becomes water dispersible.

The solubility and protein complexation are of prime importance for the utilization of the vitamin: absorption is greatly increased, infiltration into the dermal structures is facilitated and toxicity or irritation potential is almost completely eliminated, as will be further discussed in the examples below.

The compositions, RPPC, used in accordance with the methods provided by this invention are employed in effective amounts to function as an effective skin care material as well as to treat or prevent the above-described dermatological conditions. The amount of retinyl palmitate polypeptide complex may range from about 0.02 to about 5.0% by weight, preferably from about 0.2 to about 2.0%, by weight. The amount of the isoprenoid may range from about 0.01 to about 1.5%, by weight, preferably from about 0.1 to about 0.5%, by weight, of the total RPPC composition.

The RPPC composition may be formulated with a number of other stabilizers, such as antioxidants to retard auto-oxidation, e.g., butylated hydroxytoluene (BHT), butylated hydroxyanisole (BHA), or d,1, alpha tocopherol (Vitamin E); sunscreens such as para-aminobenzoic acid (PABA) and its derivatives, oxybenzone, to prevent both degradation of the retinol and provide protection to the skin against ultraviolet radiation; chelating agents, such as ethylenediamine tetraacetic acid (EDTA) and its sodium salts to prevent catalytic oxidation caused by heavy metals contaminants; preservatives such as para-hydroxy benzoic acid derivatives, diazolidinyl urea, etc., and humectants, emollients, emulsifiers, and stabilizers and fragrance.

The RPPC compositon may be employed in effective amounts in a number of useful formulations, including by way of non-limiting examples, skin lotion for photodamaged skins; skin creams for pre- and after exposure to the sun; skin creams for mild acne; and general skin care; e.g., anti-aging cream and night cream; therapeutic bath and shower gel; wind and sun protective lip-balm stick; moisturizing ointment for wind, sun and weather protection; ointment for treatment of external hemorrhoids.

The prevention invention is described below in specific working examples which are intended to illustrate the invention without limiting its scope.

EXAMPLE 1

Preparation of Retinyl Palmitate-Plant Protein Complex (RPPC)

In the fermentation vessel retinyl palmitate, U.S.P. was reacted at mildly elevated temperature of from about 30° C. to about 40° C. with an excess of finely minced carrot pulp. The reaction proceeded until no more free-state Vitamin A (retinyl palmitate) was detectable in the reaction mixture. Vitamin A was assayed by HPLC according to the procedure adopted in 1956 for international use by the International Union of Pure and Applied Chemistry USP XX. When no more free-state Vitamin A was detected in the reaction mixture, the reaction was discontinued. The suspension obtained was concentrated under vacuum, followed by spray-drying to a free-flowing, orange powder, which was determined to be a conjugate of retinyl palmitate and protein (or polypeptide) and beta-carotene.

The properties of the free-flowing, orange powder were determined as follows:

TABLE 1

| RPPC Properties | |
| --- | --- |
| Description: | Free-flowing, orange powder with characteristic odor and taste |
| Vitamin A. Content: (USP Assay Method) | Not less than 250,000 (i.u.) International Units per gram |
| Protein: (Kjeldahl N, F-6.25) | Not less than 10.0% |
| Essential Fatty Acids: | Not less than 2.5% |
| Identification: | Standard Infrared (I.R.) Spectrum |
| Moisture: | 7.0% max. |
| Total Beta Carotene Content: | Available |
| Bacteriological: | Max. 500 opg, absence of pathogens |

A series of efficacy tests were conducted using the composition obtained in Example 1.

EXAMPLE 2

In Vitro Water/Solvent Partitioning

RPPC was compared with retinyl palmitate oil, USP and Retinyl palmitate gelatin beads (Roche Laboratories, Nutley, N.J.) at both room temperature 23° C., and hot water bath, (70°C.) and in hexane extraction procedures followed by HPLC asays.

The materials used were:

| | |
| --- | --- |
| Retinyl palmitate, USP (RP) | Potency: 1.5 MM i.u./Gm |
| Retinyl palmitate gelatin beads (RPG) | Potency: 500,000 i.u./Gm |
| Retinyl palmitate polypeptide (RPPC) (Vitazyme TM A, Brooks Industries, Inc., South Plainfield, New Jersey) | Potency: 250,000 i.u./Gm |

The method s for determining in vitro water/solvent partitioning was as follows:

Individual dispersions of the above were prepared in the following solvents:

(1) Distilled water at 23° C.

(2) Distilled water at 70° C.

(3) n-Hexane at 23° C.

The dispersions were made under nitrogen and protected from light, using high shear agitation to yield particles of less than 0.5 u in diameter. The concentrations in each case were calculated to yield 4,000 i.u. per ml. The dispersions were centrifuged until clear supernatant liquids were obtained. Aliquouts of 50 uL of the clear supernatants were injected into the HPLC columns and the resulting peaks were evaluated, using a methanol solution of retinyl palmitate as the standard.

Results were obtained as follows:

TABLE 2

| | | | |
|---|---|---|---|
| (1) Water at 23° C.: | | | |
| RP and RPG: | No peak | | |
| RPPC: | Peak #1 - 0.07 | 0.076 | Absorption equivalent to 2,500 i.u. per ml |
| | Peak #2 - 0.006 | | |
| (2) Water at 70° C.: | | | |
| RP: | No Peak | | |
| RPG: | Peak #1 - 0.044 | 0.10 | Equivalent to approx. 4,000 i.u. |
| | Peak #2 - 0.056 | | |
| RPPC: | Peak #1 - 0.135 | 0.191 | Equivalent to approx. 7,640 i.u. |
| | Peak #2 - 0.056 | | |
| (3) n-Hexane at 250° C. | | | |
| RP: | Peak #1 - 0.031 | 0.10 | Equivalent to approx. 4,000 i.u. |
| | Peak #2 - 0.070 | | |
| RPG: | No peaks | | |
| RPPC: | Peak #1 - 0.047 | 0.051 | Equivalent to approx. 2,000 i.u. |
| | Peak #2 - 0.004 | | |

Discussion

RP showed no solubility in water at both 23° C. and 70° C.

RPG showed no solubility in water at 20° C., good solubility at 70° C., but no solubility in n-hexane.

RPPC showed some solubility in 23° C. water. At the high temperature, related retinoids such as beta-carotene, etc., are activated leading most likely to cleavage of the double-chain molecule and producing a very high retinyl activity. In n-hexane RP shows good solubility, while RPG is insoluble. RPPC shows partial activity, indicating adequate partitioning into both hydrophilic and lipophilic systems.

It was found that RPPC gave rise to peaks in both solvents, while retinyl palmitate oil showed no migration into water with some fractionation into hexane. Retinyl palmitate gelatin beads displayed no fractionation into hexane and exhibited partial solvency into water. This dual partitioning of RPPC makes it eminently suitable for epidermal absorption.

In contrast to retinyl palmitate, which displays strong hydrophobicity, and a physical gelatin-retinyl palmitate blend (beads) which shows hydrophilicity, but is strongly hydrophobic, the retinyl palmitate-polypeptide complex exhibits good hydrophilic properties especially at increasing temperatures as well as adequate lipophilicity.

These ambiphilic characteristics of RPPC should result in superior cutaneous absorption and effective affinity to cell membranes.

EXAMPLE 3

Skin Stripping Procedure

A standard skin stripping procedure was conducted on 10 volunteers, comparing RPPC with retinyl palmitate oil, formulated in an emulsion base. The purpose of the study was to compare the topical absorption properties of retinyl palmitate (Roche Laboratories, Nutley, N.J.) - RP - with retinyl palmitate polypeptide (Brooks Vitazyme TM A, South Plainfield, N.J.) i.e., RPPC.

Materials and Methods

Ten subjects, 4 females and 6 males, ranging in age from 18 to 27 years participated with informed consent. Each subject received 75 mg of Product A (Jergens Lotion containing 2,829 i.u./gm or 2.89 mg/gm RP, USP, Potency: 1,000,000 i.u./gm, for a total of 212 i.u. per 75 mg) and 75 mg of Product B (Jergens Lotion containing 2,678 i.u./gm or 10,712 mg/gm RPPC (Brooks Industries, Inc., South Plainfield, N.J.), potency: 250,000 i.u./gm, for a total of 201 i.u. per 75 mg).

The products were applied to alternate inner wrist surfaces, in areas of 2.5 × 1.0 cm, rubbed into the skin for aproximately 5-10 seconds, using a gloved finger as an applicator and applying equal pressure in all applications. The lotions were prepared shortly prior to use by thoroughly mixing an accurately weighed quantity of RP or RPPC with Jergens Lotion. Mixing, applications and assays were performed in subdued light in order to decrease photodecomposition. The application sites were loosely covered with protective aluminum foil. After 30 minutes of exposure, the surface products were removed by rinsing with alcohol followed by air-drying. A strip of 3M Tape was then applied to the application site in a slightly larger rectangle than the site and removed. This stripping process was repeated for a total of 15 times and was designed to removed the entire *stratum corneum*. The combined strips were eluted with methanol and the eluates were assayed for RP by HPLC, using a Lichrosorb Si 60/5 micron column, after separation and saponification according to a modified USP XXI procedure.

The percentage of absorbed RPP was calculated and the results are summarized in the following table:

TABLE 3

| Subject | % Retinyl Palmitate Absorbed | % Retinyl Palmitate Polypeptide Absorbed |
|---|---|---|
| 1. Male | 0.55 | 8.81 |
| 2. Male | 0.90 | 15.52 |
| 3. Female | 0.57 | 9.20 |
| 4. Male | 1.02 | 10.08 |
| 5. Male | 1.01 | 10.05 |
| 6. Female | 0.75 | 5.70 |
| 7. Male | 0.79 | 6.68 |
| 8. Male | 1.20 | 21.60 |
| 9. Female | 0.96 | 10.56 |
| 10. Female. | 0.67 | 6.03 |
| Average +/− Std. Deviation | 0.84 +/− 0.21% | 10.42 +/− 4.84% |

Although RPPC (Brooks, Vitazyme TM A) contains other constituents besides RP which must also have been absorbed, the assay procedure being specific for the determination of RP detected only this substance. There was no significant difference between the male and female absorption of either form of Vitamin A, although the males tended to absorb more. RPPC (Brooks, Vitazyme TM A) produced more than a tenfold greater absorption into the stratum corneum than synthetic RP, USP, the difference being highly significant (p 0.001 by a paired t-test).

Under the controlled test conditions RPPC (Brooks, Vitazyme TM A) produced a significantly greater absorption into the epidermis than RP (retinyl palmitate, USP).

EXAMPLE 4

Panel Test (Consumer Evaluation Double-Blind Study)

A panel of sixteen subjects consisting of fourteen females (ages 17 to 64) and two males (ages 14 and 17) were instructed to apply the active cream to one side of their faces and a control consisting of the vehicle without the active ingredient on the other side. Coded lotions containing 0.5% RPPC, by weight (equivalent to 0.125% retinyl palmitate, by weight), and control lotions of the same composition but without the active RPPC ingredient were used.

The products were used daily, alternating right versus left side from one subject to the other. The volunteers were instructed to apply the lotions contra-laterally to the face, on the right and left sides. The creams were used for four weeks and the members of the panel reported weekly to the laboratory for inspection. The participants were asked to grade subjectively any changes of appearance, feel and suppleness, comparing both sides of their faces.

Results

In the majority of the subjects, it became evident that after a use period of two weeks the "active" side seemed to have a somewhat clearer, fresher and more healthy appearance. The participants themselves identified the side of their face to which the active material was applied as the better side using such terms as "smoother," "clearer," "younger looking," "more vibrant," etc. This consensus was definitely confirmed at the end of the study. Most of the female participants asked for further supplies of the active cream in order to continue this beneficial treatment.

The two male subjects who had an oily complexion with some signs of incipient acne were particularly pleased since their complexions cleared and the signs of acne disappeared.

The older participants remarked that surface lines and comparatively superficial wrinkles showed almost complete disappearance. They also remarked that their complexions took on a pink coloration which they equated to a more youthful appearance.

This study indicates that RPPC (Vitazyme TM A) is a valuable ingredient for the improvement of facial complexion in both females and males.

A series of irritation tests were next carried out using RPPC.

EXAMPLE 5

Skin Irritation Tests

Under the supervision of a dermatologist, RPPC and the following test materials were repeatedly applied to the forearms of a panel of human subjects of both sexes. The test materials included:
A. Glycerin
B. RPPC 2 (Vitazyme 2)
C. RPPC 3 (Vitazyme 3)
D. Retin-A 0.01% gel
E. RPPC 1 (Vitazyme 1)
F. RPPC 4 (Vitazyme 4)
G. The control was measurement of skin water vapor loss on the untreated dorsal side of the forearm because the entire volar side was used in the treatments. It is likely that the dorsal side probably has a slightly lower skin water vapor loss than the volar side.

Results

No irritant reactions were observed with any test material. There was no significant difference between the creams and controls in skin water vapor loss.

EXAMPLE 6A

Primary Eye Irritations

The subjects, six New Zealand albino rabbits from Fab Laboratories, New City, N.Y., were fed a diet of Purina rabbit pellets. During the test period the animals were individually housed in wire bottom cages in an environmentally controlled room with a 12 hour light-/dark cycle. Feed and water were provided ad-libitum after dosing.

The procedure for determining Primary Eye Irritation was carried out as follows. (FHSLA 16 CFR 1500.42.) Six healthy young adult albino rabbits exhibiting no ocular defects or corneal defects and not previously used for any other test were released for testing. The test animals were each uniquely identified. One-tenth of a milliliter of the test material was placed on the everted lower lid of one eye of each rabbit. The upper and lower lids were gently held together for one second before releasing, to prevent loss of the test material. The contralateral eye of each rabbit remained untreated and served as a control. Ocular lesions were evaluated by the method of Draize, et al. (*J. Pharmacol. Exp. Ther.*, 83: 377–390, 1944). The Draize scores were then classified according to Kay and Calandra (*J. Soc. Cos. Chem.*, 13: 281–289, 1962). Lesions were evaluated at 24, 48 and 72 hours.

Results

Observations in the case of each rabbit were unremarkable. The test RPPC material was considered to be practically nonirritating (PN) to the eye according to the reference materials.

EXAMPLE 6B

Primary Skin Irritation Test

The subjects were six New Zealand albino rabbits from Fab Labs, New City, N.Y., were fed a diet of Purina rabbit pellets.

Environmental Conditions

During the test period the animals were individually housed in stainless steel wire bottomed cages in an environmentally controlled room with a 12 hour light/dark cycle. Feed and water were provided ad-libitum after dosing.

In this test for Primary Skin Irritation, the following procedure was used: FHSLA, 16 CFR 1500.41. Open Patch-Twenty Four Hour Exposure. The six healthy rabbits not previously used for any other test were each uniquely identified and then prepared by clipping the trunk free of hair. Five-tenths of a milliliter or 0.5 g of the test material was applied on intact skin and abraded skin on each rabbit. After 24 hours, all tests sites were wiped with a cloth to prevent further exposure. Skin lesions were evaluated at 24 and 72 hours and scored in accordance with FHSLA 16 CFR 1500.41.

Results

Observations for all six rabbit subjects were unremarkable. The test RPPC material was considered to be a non-primary irritant to the skin according to reference methods.

The following examples illustrate products for use as dermatologicals or skin care preparations in accordance with the present invention. The methods for preparing these products, including the equipment and conditions are well known to those skilled in the art.

EXAMPLE 7

Skin Lotion Preparation

A skin lotion was prepared using the RPPC of the present invention.

Skin Lotion for Photodamaged Skin

TABLE 4

|  | Range % | Preferred % | Batch of 100 kgs |
|---|---|---|---|
| Demineralized water | 50-60 | 54-58 | 56.00 |
| Magnesium aluminum silicate (Vanderbilt) | 0.1-0.5 | 0.2-0.4 | 0.30 |
| Carbomer 941, 2% dispersion (Goodrich) | 3.5-10.0 | 7.0-8.0 | 7.50 |
| Tetrasodium EDTA (Hampshire) | 0.05-0.25 | 0.08-0.12 | 0.10 |
| Propyleneglycol (and) diazolidinyl urea (and) methylparaben (and) propylparaben (Sutton) | 0.8-2.5 | 1.0-1.7 | 1.35 |
| Cetearyl alcohol (and) osteareth-20 (Amerchol) | 0.5-2.0 | 0.7-1.0 | 0.30 |
| Sorbitan stearate (Emery) | 0.25-1.0 | 0.4-0.7 | 0.50 |
| Octyldimethyl PABA (Van Dyk) | 0.3-1.0 | 0.4-0.7 | 0.50 |
| Stearic acid, triple pressed (Witco) | 0.3-1.0 | 0.4-0.7 | 0.50 |
| Glyceryl stearate (Glyco) | 0.7-1.5 | 0.8-1.2 | 1.00 |
| BHT (Eastman) | 0.02-0.10 | 0.04-0.08 | 0.06 |
| Cetyl alcohol (and) acetylated lanolin alcohol (Croda) | 0.3-1.0 | 0.4-0.6 | 0.50 |
| PPG-15 Stearyl ether (Croda) | 0.2-0.6 | 0.3-0.5 | 0.40 |
| Mineral Oil (Witco) | 1.5-4.0 | 2.5-3.5 | 3.00 |
| Cetearyl alcohol (Witco) | 0.8-2.0 | 1.2-1.8 | 1.40 |
| Potassium hydroxide pellets, USP, NF | 0.1-0.3 | 0.12-0.16 | 0.15 |
| Fragrance | 0.1-0.5 | 0.15-0.3 | 0.20 |
| Propyleneglycol (U. Carbide) | 2.0-4.0 | 2.5-3.5 | 3.00 |
| Quaternium-15 (Dow) | 0.1-0.4 | 0.15-0.25 | 0.20 |
| RPPC (Brooks) | 0.2-2.0 | 0.8-1.5 | 9.6 |
| Demineralized water | q.s ad 100 | | 1.00 |

The procedure for preparing the skin lotion for photodamaged skin was as follows:

(1) Heat water to 70° C., Disperse Veegum with high shear.
(2) Ad carbomer, EDTA and Germaben and agitate until uniform.
(3) Melt oil phase ingredients and heat to 70° C.
(4) Slowly add water phase to oil phase and agitate until uniform.
(5) Add KOH and agitate thoroughly. Start cooling at 50° C.
(6) Separately disperse RPPC in propyleneglycol with high shear, slowly add water followed by Quaternium-15.
(7) Add (6) to batch with thorough agitation.
(8) Adjust pH to 5.0-6.0 with citric acid solution.

EXAMPLE 8

Skin Cream for Pre- and After Sun Exposure, Mild Acne, General Skin Care (Anti-Aging)

TABLE 5

|  | Range % | Preferred % | Batch of 100 kgs |
|---|---|---|---|
| Demineralized water | 50-60 | 54-58 | 56.00 |
| Magnesium aluminum silicate (Vanderbilt) | 0.1-0.5 | 0.2-0.4 | 0.30 |
| Carbomer 941, 2% dispersion (Goodrich) | 3.5-10.0 | 7.0-8.0 | 7.50 |
| Tetrasodium EDTA (Hampshire) | 0.05-0.25 | 0.08-0.12 | 0.10 |
| Propyleneglycol (and) diazolidinyl urea (and) methylparaben (and) propylparaben (Sutton) | 0.8-2.5 | 1.0-1.7 | 1.35 |
| Cetearyl alcohol (and) ceteareth-20 (Amerchol) | 0.5-2.0 | 0.7-1.0 | 0.30 |
| Sorbitan stearate (Emery) | 0.25-1.0 | 0.4-0.7 | 0.50 |
| Octyldimethyl PABA (Van Dyk) | 0.3-1.0 | 0.4-0.7 | 0.50 |
| Stearic acid, double pressed (Witco) | 0.3-1.0 | 0.4-0.7 | 0.50 |
| Dimethicone (Dow Corning) | 0.1-0.3 | 0.15-0.25 | 0.20 |
| PPG-70 cetyl ether (Croda) | 1.0-3.5 | 1.5-2.5 | 2.00 |
| BHT (Eastman) | 0.02-0.10 | 0.04-0.08 | 0.06 |
| Acetylated lanolin alcohol (Amerchol) | 0.5-2.8 | 0.8-1.6 | 1.20 |
| Mineral Oil (Witco) | 1.5-4.0 | 2.5-3.5 | 3.00 |
| Cetearyl alcohol (Witco) | 0.25-1.4 | 0.4-0.8 | 0.60 |
| Potassium hydroxide pellets, USP, NF | 0.1-0.3 | 0.12-0.16 | 0.15 |
| Fragrance | 0.1-0.5 | 0.15-0.3 | 0.20 |
| Propyleneglycol (U. Carbide) | 2.0-4.0 | 2.5-3.5 | 3.00 |
| Quaternium-15 (Dow) | 0.1-0.4 | 0.15-0.25 | 0.20 |
| RPPC (Brooks) | 0.2-2.0 | 0.8-1.5 | 9.6 |
| Demineralized Water | q.s ad 100 | | 1.00 |

The procedure followed was the same as in Example 7.

EXAMPLE 9

Therapeutic Bath and Shower Gel

TABLE 6

|  | Range % | Preferred % | Batch of 100 kgs |
|---|---|---|---|
| Demin. water (Source) | q.s. ad 100 | | g.s. |
| Quaternium-41 (Merck) | 2.5-6.5 | 3.0-5.5 | 4.00 |
| Sodium C14-16 olefin sulfonate (Stepan) | 18.0-32.0 | 21.0-28.0 | 24.00 |
| Sodium myreth sulfate (Henkel) | 5.5-15.0 | 8.5-12.5 | 10.50 |
| Disodium EDTA (Hampshire) | 0.05-0.25 | 0.08-0.12 | 0.10 |
| Isostearamide DEA (Alzo) | 1.0-3.0 | 1.5-2.6 | 2.00 |
| BHA (Eastman) | 0.02-0.10 | 0.04-0.08 | 0.06 |
| Demineralized water | 0.09-0.45 | 0.06-0.10 | 0.215 |
| Phosphoric acid 85%, NF | 0.03-0.15 | 0.06-0.10 | 0.035 |
| Benzophenone-4 (BASF) | 0.05-1.0 | 0.2-0.4 | 0.30 |
| PEG-75 lanolin (Amerchol) | 0.5-3.0 | 1.0-2.0 | 1.50 |
| Fragrance | | q.s. | |
| DMDM Hydantoin (Glyco) | 0.1-0.5 | 0.15-0.30 | 0.20 |
| Propyleneglycol (U. Carbide) | 2.0-4.0 | 2.5-3.5 | 3.00 |
| RPPC (Brooks) | 0.2-2.0 | 0.8-1.3 | 1.00 |
| Demineralized water | | q.s. | |
| Color Solution | | q.s. | |
| Ammonium chloride, NF | 0.2-2.0 | 0.4-1.0 | 0.65 |
| Cocoamidopropyl betaine (Croda) | 7.0-14.0 | 9.5-11.5 | 10.50 |

The procedure for preparing the therapeutic bath and shower gel was as follows:

(1) Heat water to 60°-65° C., with agitation add Quaternium-41, followed by Olefin sulfonate. Agitate until uniform.
(2) Slowly add Sodium myrethsulfate and Disodium EDTA. Agitate.
(3) At 65° C. add Isostearamide and BHA. Agitate.

(4) Separately, prepare phosphoric acid solution, slowly add to batch. Agitate.
(5) Slowly add Cocoamidopropylbetaine and agitate until uniform. Cool to 45° C. and add Benzophenone-4.
(6) Separately warm PEG-75 lanolin to 45° C. and add fragrance oil. Agitate to uniform and add to batch.
(7) Under agitation add DMDM hydantoin.
(8) Separately disperse RPPC in propyleneglycol with high shear, slowly add water. Pass through homogenizer. Add dispersion to batch, agitate until uniform.
(9) Add color solution and ammonium chloride. Agitate until uniform while cooling to 30°–35° C.

EXAMPLE 10

Wind and Sun Protective Lip-Balm Stick

TABLE 7

|  | Range % | Preferred % | Batch of 100 kgs |
|---|---|---|---|
| BHT (Eastman) | 0.01–0.10 | 0.04–0.08 | 0.06 |
| Octyldimethyl PBA (Van Dyk) | 0.5–1.5 | 0.8–1.2 | 1.00 |
| Cocoa Butter, USP (Universal Food) | 2.5–8.0 | 3.5–6.5 | 5.00 |
| Beeswax, white (Leonhard) | 6.5–14.0 | 8.0–12.0 | 10.00 |
| Ozokerite (S.B. Penick) | 20.0–40.0 | 25.0–34.0 | 30.00 |
| Octyl dodecanol (Henkel) | 4.0–8.0 | 5.0–7.0 | 6.00 |
| White Petrolatum (Witco) | 15.0–26.0 | 18.5–23.5 | 21.65 |
| Mineral Oil (Witco) | 12.0–24.0 | 16.0–20.0 | 18.00 |
| Propylparaben (Napp) | 0.10–0.40 | 0.05–0.30 | 0.20 |
| Butylparaben (Napp) | 0.01–0.10 | 0.01–0.06 | 0.04 |
| Hydrous lanolin (Croda) | 0.6–6.0 | 2.4–4.5 | 3.50 |
| RPPC (Brooks) | 0.2–2.0 | 0.8–1.5 | 1.00 |
| Demineralized water | 1.0–3.0 | 1.2–2.3 | 1.75 |
| Flavor |  | q.s. |  |
| Color |  | q.s. |  |

Procedure
(1) Melt together all materials except last five. Agitate to clarity.
(2) Separtely disperse RPPC in hot water, add to melted lanolin, pass through roller mill.
(3) Cool (1) to 55° C., slowly add (2).
(4) Add flavor and color, pour into molds.

EXAMPLE 11

Moisturizing Ointment for Wind, Sun and Weather Protection, and also Suitable for External Hemorrhoids

TABLE 8

|  | Range % | Preferred % | Batch of 100 kgs |
|---|---|---|---|
| Stearyl alcohol (Emery) | 20–30 | 24–26 | 25.0 |
| White Petrolatum (Witco) | 20–30 | 24–26 | 25.0 |
| Sodium lauryl sulfate (Stepan) | 0.4–2.4 | 0.8–1.2 | 1.0 |
| Methylparaben (Napp) | 0.08–0.1 | 0.12–0.18 | 0.15 |
| Propylparaben (Napp) | 0.01–0.10 | 0.03–0.08 | 0.05 |
| Propyleneglycol (U. Carbide) | 8.0–18.0 | 10.0–14.0 | 12.00 |
| RPPC (Brooks) | 0.2–2.0 | 0.8–1.5 | 1.00 |
| Demineralized water | 26.0–42.0 | 30.0–38.0 | 34.00 |
| d,l Alphatocopherol (Roche) | 0.2–2.0 | 0.4–0.6 | 0.50 |
| Octyldimethyl PABA (Van Dyk) | 0.5–1.5 | 0.8–1.2 | 1.00 |

Procedure
(1) Melt steryl alcohol, Petrolatum and Octyldimethyl PABA at 75° C., agitate until uniform.
(2) Dissolve parabens in propyleneglycol.
(3) Disperse RPPC in propyleneglycol solution with high shear, slowly add 10% of the required amount of water, pass through homogenizer.
(4) At 50°–55° C. (3) to (1) followed by balance of water. Cool with constant agitation, pass batch through roller mill.

The above examples should not be considered as restrictive to the products enumerated. They can be readily expanded as necessary to prepare other topical products, using other ingredients, additives, stabilizers, enhancers and the like by those skilled in the art. Using the principles as taught, products for the protection and general improvement of hair, nails, tissues surrounding the eye as well as for mucous membranes can be easily formulated.

What is claimed is:

1. A method of treating photo damaged skin in a human comprising
applying to the affected area of said skin an effective amount of ca composition comprising
an extract from yellow or deep green vegetables wherein said extract is characterized by the presence of retinoid binding polypeptides having molecular weight of about 5000 to about 7000 daltons,
at least one retinyl fatty acid ester bound to said polypeptides forming a retinyl ester polypeptide complex, and
an isoprenoid.

2. A method of protecting or treating the skin of a human against the abrasive effects of wind comprising
applying to the area of said skin to be protected or treated an effective amount of a composition comprising
an extract from yellow or deep green vegetables wherein said extract is characterized by the presence of retinal binding polypeptides having molecular weight of about 5000 to about 7000 daltons,
at least one retinyl fatty acid ester bound to said polypeptides forming a retinyl ester polypeptide complex, and
an isoprenoid.

3. A method of moisturizing skin in a human comprising
applying to the area of said skin to be moisturized an effective amount of a composition comprising
an extract from yellow or deep green vegetables wherein said extract is characterized by the presence of retinal binding polypeptides having molecular weight of about 5000 to about 7000 daltons,
at least on retinyl fatty acid ester bound to said polypeptides forming a retinoid ester polypeptide complex, and
an isoprenoid.

4. The method of claim 1, which comprises applying said composition wherein said extract is derived from the group consisting of carrots, squash, pumpkins, and spinach, or a combination of any of the foregoing.

5. The method of claim 4, wherein said extract is derived from carrots.

6. The method claim 1, which comprises applying said composition wherein said isoprenoid comprises a carotenoid.

7. The method of claim 6, wherein said carotenoid comprises beta-carotene and said retinoid comprises retinyl-palmitate.

8. The method of claim 1, which comprises applying said composition wherein said retinyl ester-polypeptide complex comprises from about 0.02% to about 5.0%, by weight, of the total composition.

9. The method of claim 1, which comprises applying said composition wherein said isoprenoid comprises from about 0.01% to about 1.5% by weight, of the total composition.

10. The method of claim 1, which comprises applying said composition 1-4 times per day.

11. The method of claim 2, which comprises applying said composition wherein said extract is derived from the group consisting of carrots, squash, pumpkins, and spinach, or a combination of any of the foregoing.

12. The method of claim 11, wherein said extract complex is derived from carrots.

13. The method of claim 2, which comprises applying said composition wherein said isoprenoid comprises a carotenoid.

14. The method of claim 13, wherein said carotenoid comprises beta-carotene and said retinoid comprises retinyl palmitate.

15. The method of claim 2, which comprises applying said composition wherein said retinyl ester retinoid-polypeptide complex comprises from about 0.02% to about 5.0%, by weight, of the total composition.

16. The method of claim 2, which comprises applying said composition wherein said isoprenoid comprises from about 0.01% to about 1.5% by weight, of the total 17. The method of claim 3, which comprises applying said composition wherein said polypeptide complex is derived from the group consisting of carrots, squash pumpkins, and spinach, or a combination of any of the foregoing.

18. The method of claim 3, wherein said polypeptide complex is derived from carrots.

19. The method of claim 3, which comprises applying said composition wherein said isoprenoid comprises a carotenoid.

20. The method of claim 19, wherein said carotenoid comprises beta-carotene and said retinoid comprises retinyl palmitate.

21. The method of claim 3, which comprises applying said composition wherein said polypeptide complex comprises from about 0.02% to about 5.0%, by weight, of the total composition.

22. The method of claim 3, which comprises applying said composition wherein said isoprenoid comprises from about 0.01% to about 1.5%, by weight, of the total composition.

23. The method of claim 3, which comprises applying said composition 1-4 times per day.

* * * * *